United States Patent [19]

Rodgers et al.

[11] 4,341,124
[45] Jul. 27, 1982

[54] AUTOMATIC SAMPLING APPARATUS

[75] Inventors: Douglas N. Rodgers; Manfred Siegler; David Y. H. Shen, all of San Jose, Calif.

[73] Assignee: General Electric Company, San Jose, Calif.

[21] Appl. No.: 205,414

[22] Filed: Nov. 10, 1980

[51] Int. Cl.³ ............................................. G01N 1/10
[52] U.S. Cl. .............................. 73/863.01; 73/863.23; 73/863.43
[58] Field of Search ........... 73/863.01, 863.03, 863.23, 73/863.25, 863.31, 863.43, 863.61

[56] References Cited

U.S. PATENT DOCUMENTS

| | | |
|---|---|---|
| 3,348,418 | 10/1967 | Ulting . |
| 3,457,787 | 7/1969 | Maattsch .......................... 73/863.02 |
| 3,468,166 | 9/1969 | Putman .................................. 73/864 |
| 3,524,351 | 8/1970 | Bayly et al. . |
| 3,751,991 | 8/1973 | Fisher et al. . |
| 3,985,028 | 10/1976 | Yoshida . |
| 4,037,475 | 7/1977 | Topham ........................... 73/863.01 |
| 4,167,875 | 9/1979 | Meakin . |

FOREIGN PATENT DOCUMENTS 2641801  2/1978  Fed. Rep. of Germany .

Primary Examiner—S. Clement Swisher
Attorney, Agent, or Firm—Ivor J. James, Jr.; Robert P. Sabath; Samuel E. Turner

[57] ABSTRACT

An automatic sampling apparatus for particles suspended in liquid, which maintains particles in suspension by periodically directing and redirecting the liquid first down one branch of a manifold and then down another, and which selectively directs the liquid toward one or more of a plurality of filters, engaging in both operations under the direction of a programmable process controller. Liquid flow rate through the filters is metered, providing information regarding flow rate and volume to the process controller. A minimum of manual handling is required and user exposure to the sampling environment, which may be radioactive, is reduced.

13 Claims, 1 Drawing Figure

AUTOMATIC SAMPLING APPARATUS

BACKGROUND OF THE INVENTION

This invention relates to an automatic sampling apparatus for collecting a plurality of samples of liquid suspended particles, particularly radioactive particles, such as those found in the liquid stream of a nuclear reactor. The concentration of certain corrosion products contained in the liquid is thereby determinable. Since plural samples are collected during operation, a minimum in manual handling is required and user exposure to radiation is accordingly reduced. The particles are maintained in suspension by periodically switching flow between branches of a manifold leading to a filter array.

Various kinds of sampling and filtration devices have been in use for some time. Some of these are able to obtain a plurality of samples in one operational cycle. An example of a device for rapidly acquiring and filtering a plurality of samples is disclosed in U.S. Pat. No. 4,167,875.

Although the known filter devices, including the one set forth in U.S. Pat. No. 4,167,875, do provide for useful and satisfactory results in some cases, none is specifically adapted to minimize manual handling of the samples collected in a manner and to the extent made possible by the present invention. Furthermore, none of the prior art sampling devices is specifically adapted to the sampling of solids suspended in feedwater of a steam system or in the reactor water of a nuclear power plant so as to minimize the amount and probability of the suspended particles being deposited within the filtration or sampling apparatus.

Accordingly, a primary object of the present invention is to provide an automatic sampling apparatus for maintaining solids to be sampled in liquid suspension throughout a sampling cycle.

Another object of the present invention is to provide an automatic sampling apparatus which minimizes the accumulation of solid particles within the sampling apparatus.

Another object of the present invention is to provide an automatic sampling apparatus for radioactive solids suspended in the reactor water of a nuclear power generating plant which minimizes the need for manual removal and replacement of sampling filters during operation and thereby reduces user exposure to radiation.

Another object of the present invention is to provide an automatic sampling apparatus having an automatically controllable plurality of valves for directing flow to a plurality of sampling filters.

Another object of the present invention is to provide an automatic sampling apparatus which includes a process controller for directing the operation of the automatic sampling apparatus and which is selectively programmable to determine the sequence and period of operation for valves and other components of the sampling apparatus.

Another object of the present invention is to provide an automatic sampling apparatus able to display information visually regarding the liquid flow rate and volume, and to provide feedback information to a process controller for directing the operation of the automatic sampling apparatus.

Another object of the present invention is to provide an automatic sampling apparatus for reducing equipment maintenance, improving productivity, and diminishing the likelihood of human error in controlling sampling operation.

SUMMARY OF THE INVENTION

The present invention, in accordance with one embodiment thereof, relates to an automatic sampling apparatus for solid particles flowing in a liquid stream. The apparatus effectively obtains samples by directing the liquid through one or more of a plurality of filters connected in parallel as an array. The particles are maintained in suspension in the liquid by alternately directing the stream through opposite branches of a manifold, which conducts the liquid toward selected sampling filters. A programmable process controller, including elements such as for example electric circuitry and a microprocessor, directs the liquid flow to a selected one or more filters based upon information from a flow rate meter set downstream from the filter array.

BRIEF DESCRIPTION OF THE DRAWING

The invention will be better understood from the following description taken in conjunction with the accompanying drawing, wherein.

DESCRIPTION OF THE PREFERRED EMBODIMENT

Figure 1:
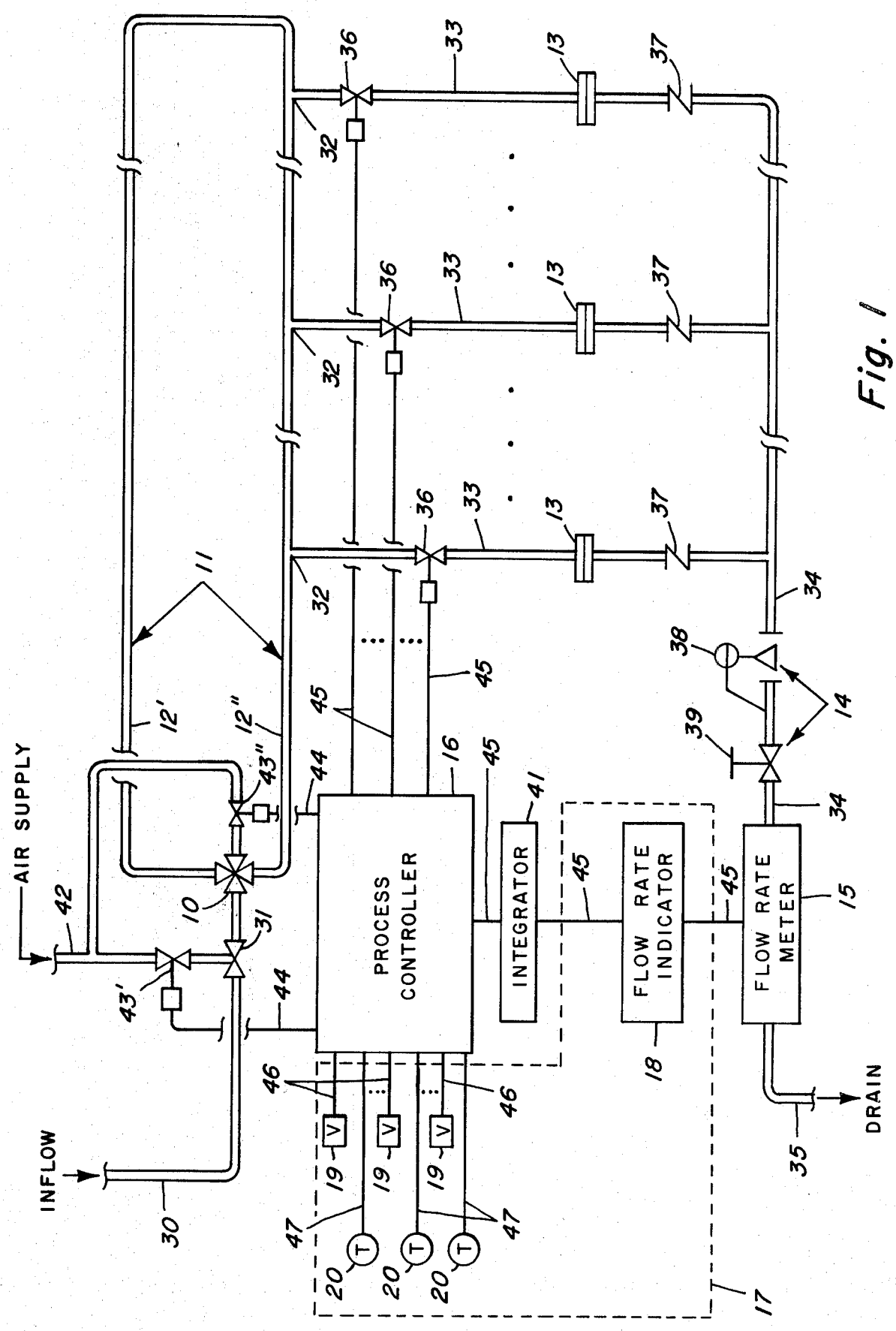
FIG. 1 is a schematic illustration of one embodiment of the present invention comprising an automatic sampling apparatus, including manifold means for directing a stream of liquid to one at a time of a plurality of filters for obtaining samples of solid particles in the stream.

Turning now to a consideration of the drawing, the automatic sampling apparatus shown in FIG. 1 comprises a system including a switching valve 10, a manifold generally designated 11 and defining an internal channel having two branches 12' and 12", and a plurality of filters 13—all of these elements being interconnected by suitable tubing.

Downstream from the filters 13 is a plurality of flow regulation devices 14 and a flow rate meter 15 to be discussed in greater detail below. In addition to the switching valve 10, the system includes other valves that will be described below and these, including the switching valve 10, are controlled by a process controller 16 according to a program of predetermined instructions. The flow rate member 15 electrically provides information to the process controller 16 on the rate of liquid flow through the filters 13, enabling implementation of the program of predetermined instructions. Information on flow rate, total flow volume, and flow time through each filter, is visually displayed on a console 17 on which are mounted a flow rate indicator 18, flow volume counters 19, and time counters 20.

Liquid enters the apparatus during sampling operation through an input tube or pipe 30 leading to an input valve 31 and the switching valve 10 for alternately directing the liquid flow to branches 12' and 12" of the manifold 11. From openings 32 in the manifold 11, a plurality of filter tubes 33 guide the liquid through the filter 13 to a common channel 34 leading to a drain 35 or the like. Each filter 13 is associated with a filter flow control valve 36 which precedes it in the direction of flow, and a check valve 37 which prevents backwash or reverse flow through the filter 13.

The common channel 34 leads the flow of liquid through a downstream pressure regulator 38 for maintaining a relatively constant flow rate. A flow control valve 39 in the common channel 34 insures that a relatively constant flow volume proceeds through the channel 34. Additionally, the flow rate meter 15 accurately measures the rate of liquid flow which leaves the sampling apparatus through the drain 35.

Electrically connected to the flow rate meter 15 is the flow rate readout or indicator 18 which visually displays the rate of flow measured by the flow rate meter 15. The indicator 18 also modifies the signal produced by the meter 15 to make it acceptable to an integrator 41, which incrementally adds flow rate over time and thereby converts flow rate into total flow volume.

The process controller 16 receives the integrated information regarding flow volume and shuttles it to the appropriate volume counter 19 to provide a permanent visual display or record as to how much liquid passed through each filter 13. As noted above, the volume and time counters, respectively 19 and 20, each of them associated with a particular filter 13, are mounted in the console 17. According to a predetermined sequence or combination, a controller 16 simultaneously switches all the associated elements, including volume counter 19, time counter 20, and filter control valve 36, "on" and "off" at the same appropriate instant of time. The process controller 16 accordingly orchestrates the movement of liquid through selected sampling filters 13 downstream from the manifold 11. The process controller 16 may include a microprocessor and associated circuitry, and can be reprogrammed for different applications involving different time cycles and flow rates.

The input valve 31 and the switching valve 10 are operated by pressurized air from the air supply 42 through respective solenoid valves 43' and 43". The process controller 16 governs the air to the input valve 31 and the switching valve 10 by suitable electric signals along electric wiring 44. Additionally, the process controller 16 governs the filter control valves 36 by similar electric wiring 45.

The preferred number of filters 13 and associated elements such as filter tubes 33 is twenty. However, any number of filters 13 may be utilized, and the fact that twenty filters are employed in this embodiment should be taken only as exemplary of the large number of filters that may be incorporated into the sampling apparatus. The drawing shows only three of the twenty filters 13 and associated elements of the instant embodiment; the remainder of the twenty filters 13 are understood to lie between the broken lines in the drawing and in parallel with filters 13 and valves 36, 37.

Each of the filters 13 includes a flat, permeable piece of material for collecting particles, which may be a round sheet or screen of natural or man-made material, as for example paper. Each filter 13 additionally includes a filter holder (not shown) including two sides for holding a permeable filter piece therebetween. An example of such a holder is noted in Table 1.

The various tubes discussed herein are made of material capable of surviving the harsh radioactive and thermal conditions to which they might be subjected in a reactor system. Within these constraints, the tube material may be plastic or metallic and is preferably stainless steel. The manifold 11 discussed above is also formed of stainless steel or another suitable metal or plastic. In particular, the tube fittings noted in Table 1 may be utilized.

Examples of the type of components may be utilized in the invention disclosed herein are shown in Table 1 below. Other or similar models may conveniently be substituted by one skilled in the art.

TABLE 1

| | |
|---|---|
| Input valve 31 | SS-42S4-131SR-NC by Whitey Company |
| Solenoid valve 43' | HT8302C26-F by Automatic Switch Co. |
| Switching valve 10 | SS-42XS4-151DA by Whitey Company |
| Solenoid valve 43" | HT8344-45 (ASCO) by Automatic Switch Co. |
| Manifold 11 | "Swagelock" tube fittings by Crawford Fitting Co. |
| Filter flow control valve 36 | V52HDBZ1252 by Skinner Precision Industries, Inc. |
| Filter paper 13 | Millipore Corporation |
| Filter holder 13 | XX45-025-00 by Millipore Corporation |
| Check valves 37 | 259-T-1-1PP by Circle Seal Co. |
| Downstream pressure regulator 38 | IR402-5-025-PM by Veriflow Corporation |
| Flow control valve 39 | SS-2R54-A by Whitey Co. |
| Flow rate meter 15 | FTM-N1-LJ5 by Flow Technology |
| Flow rate indicator 18 | SR1-2AA 2H/L by Flow Technology |
| Integrator 41 | 7501-278 by Action Instruments |
| Volume counters 19 | F2-3106 by Redington Counters, Inc. |
| Microprocessor 16 | WP6000 by Minarik Electric Co. |

In operation, the liquid to be sampled is conducted through the sampling apparatus by pressure from the sampled system applied at the input valve 31. The pressure propels the liquid through the manifold 11, one or more selected filter tubes 33, a filter flow control valve 36, and filter 13, whereby particles suspended in the liquid are deposited on the surface of permeable material in the filter 13.

The switching valve 10 directs the liquid flow down first one branch, say 12', and then down the other branch 12" of the manifold 11. At steady state, both branches 12', 12" of the manifold 11 are filled with liquid. During a first period of time, a positive flow of liquid travels down one branch; and a zero flow, down the other. During the following period of time, the flow conditions in the branches are reversed: no flow occurs down the first branch, and a positive flow travels down the other branch.

For each of these flow periods and for a substantial number of flow periods thereafter, liquid departs from the manifold 11 through the same selected opening 26. However, after having switched from one branch to the other for considerable number of periods, while departing through the same opening 32, the time will arrive at which a given filter 13 is saturated with particles, and the flow is accordingly redirected through another opening 26 by action of the process controller 16. When the flow is thus transferred from one opening 32 to another, the portion of the manifold channel between the original opening 26 and the transferred opening 32, experiences a reversal of flow direction.

The sudden, jerking, and turbulent motion of liquid thereby periodically established within the manifold 11 serves not only to maintain any solids in the liquid stream in suspension, but it dislodges particles already accumulated at various kinetically stagnant regions within the liquid sampling apparatus.

The amount of time dedicated to flow through a given filter 13 is variable. It depends in part upon the expected particle concentration in the water being sampled. For example, the concentration of suspended solids expected in the recirculating reactor water of a boiling water reactor is much higher than in the feedwater of a steam system. The particle concentration in recirculating reactor water may vary from 50 to 500 parts per billion, whereas the concentration of particles in feedwater may vary from about 1 to 10 parts per billion. To accumulate a given amount of particles from feedwater will accordingly take much more time than from reactor water.

Conversely, the process controller determined time period set for receiving liquid by a given filter is much shorter in reactor water than feedwater. A typical operating period for each filter in the case of feedwater is one or two days, and during this time the switching valve 10 may alternate flow between branches 12' and 12" at a rate of about once per hour. For reactor water, the period is typically 15 minutes to 1 hour and the switching valve may alternate flow every 3 minutes.

The process controller 16 can accordingly be preset to allocate a fixed block of time to each filter 13 for receiving liquid. This predetermined interval can be established subject to restriction upon occurrence of certain conditions. For example, if the liquid exceeds certain temperature limits, or if pressure at certain critical points in the sampling apparatus drops below or exceeds certain predetermined values, the period of time through a given filter can be abbreviated.

The check valve 37 immediately downstream from each filter 13 prevents back-pressure from dislodging particles captured on a filter 13. Even further downstream, the pressure regulator 38 maintains constant pressure downstream from the filter 13 for keeping the rate of liquid flow substantially constant. The flow control valve 39 permits fine manual control over flow volume in the common channel 34 under constant pressure. The flow rate meter 15 operates with a bladed turbine or rotor (not shown) for generating low voltage current pulses in a magnetic pick-off coil located adjacent to the rotor.

The pulsed electric signal from the flow rate meter 15 is amplified and visually displaced by the flow rate indicator 18, which shows the rate of liquid flow through the flow rate meter 15. The integrator 41 incrementally sums the rate of flow information to calculate total flow volume through the common channel 34. Suitable electric wiring 45 interconnects the meter 15, indicators 18, the integrator 41, and the process controller 16, in order to insure that the flow rate information, duly converted into flow volume information, is properly registered in the volume counters 19.

More particularly, the flow volume information is shuttled through suitable electric wiring 46 from the process controller 16 to the volume counter 19 associated with the filter in use at that given instant of time. An associated time counter 20 operates from line power (not shown) under supervision of the process controller 16 and along suitable electric wiring 47, which turns the time counter 20 on during the appropriate time, when the associated volume counter 19 and filter control valve 36 are in operation. In other words, there is a particular counter 19 that shows the total flow through any given filter 13 at a particular time. The corresponding time counter 20 provides current information as to the flow time through the given filter 13 whenever it is desired.

In summary, the automatic sampler apparatus disclosed herein has the capability of collecting plural samples of solid particles suspended in liquid without significantly exposing plant personnel to unnecessary radiation. The apparatus additionally collects particles in an arrangement that keeps the particles suspended in liquid during sampling operation.

After reference to the foregoing, modifications of this invention may occur to those skilled in the art. However, it is to be understood that this invention is not intended to be limited to the particular embodiment shown and described herein, but is intended to cover all modifications coming within the spirit and scope of the invention as claimed.

What is claimed is:

1. An automatic sampling apparatus for obtaining a plurality of samples of particles in liquid comprising:
   a plurality of filters;
   a manifold including two branches carrying liquid holding particles;
   means for transferring said liquid into said manifold;
   means for selectively carrying said liquid from said manifold through one or more of said filters; and
   switching means effective to direct liquid through first one and then the other of said two branches of said manifold, whereby suspended solids are prevented from settling in said manifold.

2. The invention of claim 1, whereby said means for selectively carrying liquid include a plurality of tubes each connecting a filter to said manifold, a filter control valve in each of said tubes, and means for selectively operating said valves to control the flow of liquid through said valves.

3. The invention of claim 1, wherein each of said filters comprises a permeable piece of filter material and includes a structure for supportively holding said permeable piece against the direction of flow, whereby liquid passes through said filter material and deposits solid particles thereupon.

4. The invention of claim 1, further comprising means for metering flow rate downstream from said plurality of filters and providing information indicative of flow rate to a process controller, and means providing a visual display of flow rate.

5. The invention of claim 4, further comprising a means for controlling both said switching valve and said means for selectively carrying said liquid from said manifold in accordance with a program of predetermined instructions.

6. The invention of claim 1, further comprising pressure regulation means for maintaining liquid pressure within a predetermined range downstream from said plurality of filters.

7. The invention of claim 1, wherein said directing of liquid through first one and then the other of said two branches of said manifold occurs periodically at substantially regular intervals.

8. The invention of claim 5, wherein said means for controlling includes a microprocessor.

9. The invention of claim 1, wherein the number of filters is 20.

10. The method of keeping solid particles suspended in liquid in a sampling apparatus comprising the steps of providing the liquid to a switching valve at the entrance of a manifold having two branches, and periodically exclusively directing the flow from the switching valve down one and then the other of the branches of the manifold.

11. The method of claim 10, further comprising the step of removing the liquid from the manifold at first one outlet of said manifold and then at another outlet of said manifold.

12. An automatic sampling apparatus for obtaining a plurality of samples of particles in liquid comprising:
   a source of liquid containing suspended radioactive particles;
   a plurality of filters;
   a manifold including two branches for carrying liquid containing suspended radioactive particles;
   means for transferring liquid from said source to said manifold;
   means for selectively carrying said liquid from said manifold through one or more of said filters; and
   switching means effective for directing liquid through first one and then the other of said two branches of said manifold;
   whereby suspended radioactive particles are prevented from settling in said manifold.

13. The invention of 12, wherein the concentration of radioactive particles in said liquid is in the range of 1 to 500 parts per billion.

* * * * *